US006929649B2

(12) United States Patent
Pugh

(10) Patent No.: US 6,929,649 B2
(45) Date of Patent: Aug. 16, 2005

(54) LANCING DEVICE WITH AUTOMATIC STICK AND RETURN

(75) Inventor: Jerry T. Pugh, Mountain View, CA (US)

(73) Assignee: LifeScan, Inc., Milpitas, CA (US)

( * ) Notice: Subject to any disclaimer, the term of this patent is extended or adjusted under 35 U.S.C. 154(b) by 499 days.

(21) Appl. No.: 10/131,724

(22) Filed: Apr. 23, 2002

(65) Prior Publication Data

US 2003/0199912 A1 Oct. 23, 2003

(51) Int. Cl.$^7$ ............................................. A61B 17/32
(52) U.S. Cl. ...................................... 606/182; 606/181
(58) Field of Search ................................. 606/181, 182, 606/185, 188, 171; 600/583; 604/164, 164.12

(56) References Cited

U.S. PATENT DOCUMENTS

| | | | |
|---|---|---|---|
| 4,924,879 A | | 5/1990 | O'Brien |
| 5,029,583 A | * | 7/1991 | Meserol et al. ............. 606/182 |
| 5,196,025 A | | 3/1993 | Ranalletta et al. |
| 5,304,193 A | | 4/1994 | Zhadanov |
| 5,527,334 A | | 6/1996 | Kanner et al. |
| 5,554,166 A | | 9/1996 | Lange et al. |
| 5,938,679 A | | 8/1999 | Freeman et al. |
| 6,206,901 B1 | * | 3/2001 | Rutynowski et al. ....... 606/182 |

OTHER PUBLICATIONS

Chapman, "The Management of Pain" $2^{nd}$ Edit. vol. 1, p. 122–132 (1990).

* cited by examiner

Primary Examiner—Julian W. Woo
(74) Attorney, Agent, or Firm—Carol M. LaSalle; Bozicevic, Field & Francis LLP

(57) ABSTRACT

A lancing device with automatic stick and lance return features is disclosed. A drive mechanism within the unit comprises a slider-crank linkage combination. It is biased by a spring member to cause automatic firing once a crank member advanced by a user causes movement of an internal linkage member beyond its fully-cocked position. After firing, the lance is withdrawn so as not to pose a threat of secondary injury to the user. In use, the device is substantially silent though its course of operation. Yet, its configuration lends itself to producing a very quick, virtually painless stick with minimal recoil or shock to the device.

22 Claims, 5 Drawing Sheets

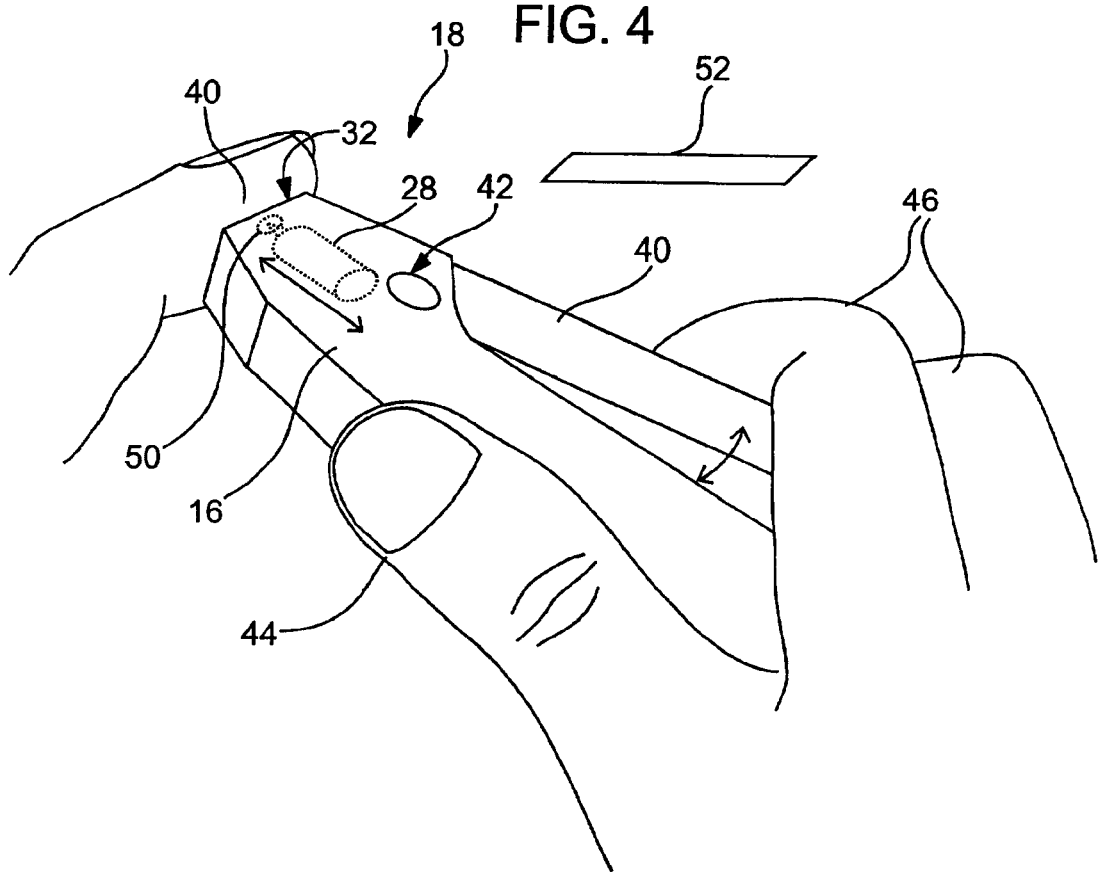

LANCING DEVICE WITH AUTOMATIC STICK AND RETURN

FIELD OF THE INVENTION

This invention relates to systems for obtaining physiologic fluid samples. More particularly, a lancing device for obtaining blood samples with minimum user discomfort is disclosed.

BACKGROUND OF THE INVENTION

Numerous lancing mechanism for obtaining blood samples have been developed. Many of these are optimized for effectiveness in quickly sticking a user with a lancing pin or blade to reduce the sensation of physical pain. Whether intentional or not, others are also designed in a manner that reduces physiological factors associated with obtaining a blood sample.

One such factor contributing to physiological discomfort in using known lancing mechanism results from loud slapping or popping noises certain devices make upon actuation. Another negative stimulus often noticed by users is recoil or sudden motion of the housing of a lancing device associated with lance firing. Anticipation of the noise or jolting motion of a lancing device can be as disconcerting as the needle stick itself. As observed by a Dr. Chapman, "Pain is far from being and emotionally neutral experience; it is almost always accompanied by emotional disturbance and distress. The physiologic accompaniments of such arousal vary with individual, but that may interact powerfully with the sensory mechanism of pain to exacerbate the pain state." Chapman, *The Management of Pain*, $2^{nd}$ Edition, Vol. 1, pg. 122 (1990).

Certain lancing devices are configured in such a way that they should run silently. Examples include those found in U.S. Pat. Nos. 4,924,879; 5,196,025; 5,304,193 and 5,938,679. These employ linkage or lever type mechanisms that advance and retract a lance without impulse loading or impact by or on the lance against opposing mechanism to cause serious noise. Other devices, even some employing camming or linkage mechanisms (such as in U.S. Pat. Nos. 5,527,334 and 5,554,166) do not.

As for the device described in U.S. Pat. No. 4,924,879 to O'Brien, it discloses a lancet driven and retracted into a cocked position by 180° oscillation of a torsion spring driven crank wheel attached to a connecting rod secured to a blade carrier constrained to slide in and out relative to an internal housing portion. A significant disadvantage of this system is presented by the fact that returning the mechanism to a cocked position results in the lance blade extension where it might present a danger in spite of an external housing provided to facilitate finger positioning. Cocking the mechanism is accomplished by a winding handle that winds a torsion spring one-half turn. A catch locks the loaded assembly until it is released by pressing a button. If cocked ahead of time, the system also presents the safety hazard of inadvertent misfire.

Similar hazards with respect to potential misfire due to stored energy in a cocked position are presented in the use of the devices described in U.S. Pat. Nos. 5,196,025 and 5,304,193. Each device utilizes a lever or linkage system that is flexed one way and then another to, respectively, fire and retract a lance member upon release from a cocked position by a latch.

The system described in U.S. Pat. No. 5,938,679 to Freeman, et al. includes an actuator having a crank wheel or link (referred to as a cam) and a connector link (referred to or pivotal arm) like the O'Brien device, but the wheel/link run in a full circle to actuate a blade assembly. The patent fails to disclose further structural details of the actuator. It does, however, describe a use where it moves an attached blade structure to penetrate and remain in a wound site for a preset length of time to fill a capillary tube associated with the blade and then retract. Such an actuator differs functionally from that of the present invention, which is intended to stick a patient and immediately retract to minimize pain. An actuator according to the present invention is not physically capable of such action or control.

It does, however, provide an exceptionally inexpensive, durable and easy to use means of actuating a lance. All this is accomplished in a smooth-operating, substantially noise free device, distinguishing the present invention over other know systems as well.

SUMMARY OF THE INVENTION

The present invention comprises a lancing device with automatic stick and lance return features once a user has cocked the device. A drive mechanism within the unit comprises a slider-crank linkage combination in the form of a crank member, a coupler link and a reciprocating lance-carrying member/slider. The drive mechanism is biased by a spring member to cause automatic firing once the crank member over-runs an equilibrium point of the spring. Any of a variety of spring types or linkage configurations may be employed. In addition, component placement may vary widely while still achieving the intended function.

Prior to cocking the device for firing, the spring preferably sets the position of the lance or lance carrier at a partially retracted position so that a tip of the lance does not pose a safety hazard. The system is preferably configured so that this position substantially coincides with a minimum energy state for the device alleviating risk of lancet misfire. A clutch may be provided in the system, typically at the crank pivot. The drive may be actuated by any number of approaches. However, a ratchet-type mechanism is most preferred.

The present invention further includes systems comprising any of these features described herein. Methodology described in association with the devices disclosed also forms part of the invention. The invention also comprises such hardware and methodology as may be used in connection with that described which is incorporated by reference.

BRIEF DESCRIPTION OF THE DRAWINGS

Each of the following figures provide examples diagrammatically illustrating aspects of the present invention. Variation of the invention from that shown in the figures is contemplated. Like elements in the various figures are often indicated by identical numbering. For the sake of figure clarity, however, some such numbering is omitted.

FIG. 4 is a perspective view of a lancing device according to the present invention in the process of being actuated by a user.

DETAILED DESCRIPTION OF THE INVENTION

Figure 1A:
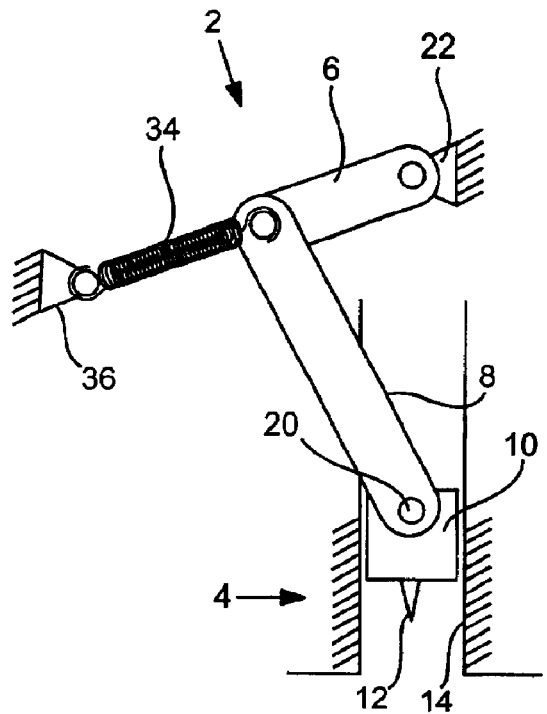
FIGS. 1A through 1E are front view of the inventive lancing mechanism in various stages of operation.

Before describing variations of the present invention in detail, first, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims made herein. Also, it is contemplated that any optional feature of the inventive variations described herein may be set forth and claimed independently, or in combination with any one or more of the features described herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are described. All existing subject matter mentioned herein (e.g., publications, patents, patent applications and hardware) is incorporated by reference herein in its entirety. The referenced items are provided solely for their disclosure prior to the filing date of the present application. Nothing herein is to be construed as an admission that the present invention is not entitled to antedate such material by virtue of prior invention.

Also, it is noted that as used herein and in the appended claims, the singular forms "a," "and," "said" and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely," "only" and the like in connection with the recitation of claim elements or the use of a "negative" claim limitation(s).

Turning now to FIGS. 1A–1E, the basic operation of a drive mechanism 2 for a lancing apparatus is shown in various stages of operation. First, the constituent parts will be described, then their sequence of motion.

Drive mechanism 2 is generally referred to as a slider-crank linkage. It comprises a slider portion 4 a crank member 6 and a coupler link 8. The slider portion includes a shuttle 10 in the form of a lance-carrying member. As shown in FIGS. 1A–1E, this member actually includes a lance tip or blade 12. The shuttle/lance-carrying member 10 is preferably confined in a channel or way 14. As configured, the channel permits only reciprocal, rectilinear movement. It is easily formed integrally with housing 16 of a complete lancing device or apparatus 18 as shown in FIG. 4, for instance, by injection molding to minimize cost. Alternate manners of directing the lance or lance tip may also be employed. Exemplary options include, another link, track, ridge or a linear bearing setup.

Figure 2:
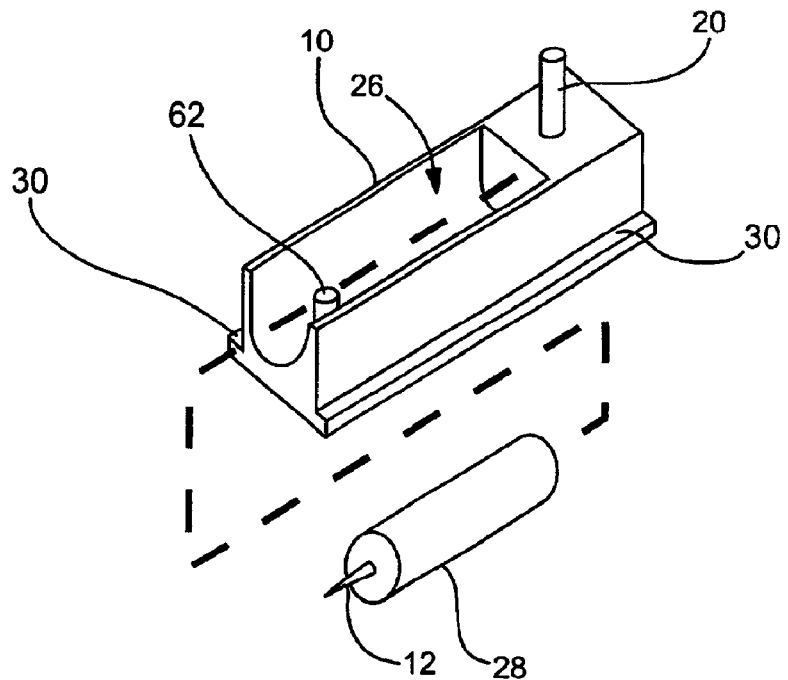
FIG. 2 is a perspective view of an alternate lancing members.

Shuttle 10 is rotably connected to coupler link, preferably by a simple pin 20. The coupler link is also rotably attached to crank member 6 via a pin 20. In a most basic variation of the invention, the crank member is rotably fixed to a crank support 22 such as device housing 16 by a pin 20. If each of the members are not to be held together by adjacent or opposing material faces in the lancing device housing, the pins may include a groove to receive a C-clip or snap ring instead. A further alternative construction could employ snap together molded parts, shoulder bolts or capped pins press fit into either of the crank, coupler or shuttle. If a connector pin 20 is to be press fit in a member as shown in FIG. 2, the member receiving the same preferably comprises a lubricious material irrespective of how the pin is configured.

In a preferred embodiment of the invention, the connection at the crank member includes a one-way clutch 54 as may be purchased in the form of one-way cartridge bearings rather that a rotably unconstrained interface. Suitable clutch members are well known in the art. An exemplary type is commonly known as an "overrunning clutch" and illustrated in connection with FIG. 3. Such a device may also be regarded as a form of ratchet. When driven clockwise as shown in the figure, rollers or balls 56 are free to move within tapered recesses 58 and the device spins freely. When counter-rotated, the balls are wedged within the tapered recesses between the anchored center 60 and outer wheel member 6. The purpose of including a clutch is to remove oscillations from the system or prevent inadvertent unwinding from a cocked position instead of firing the lance.

Figure 3:
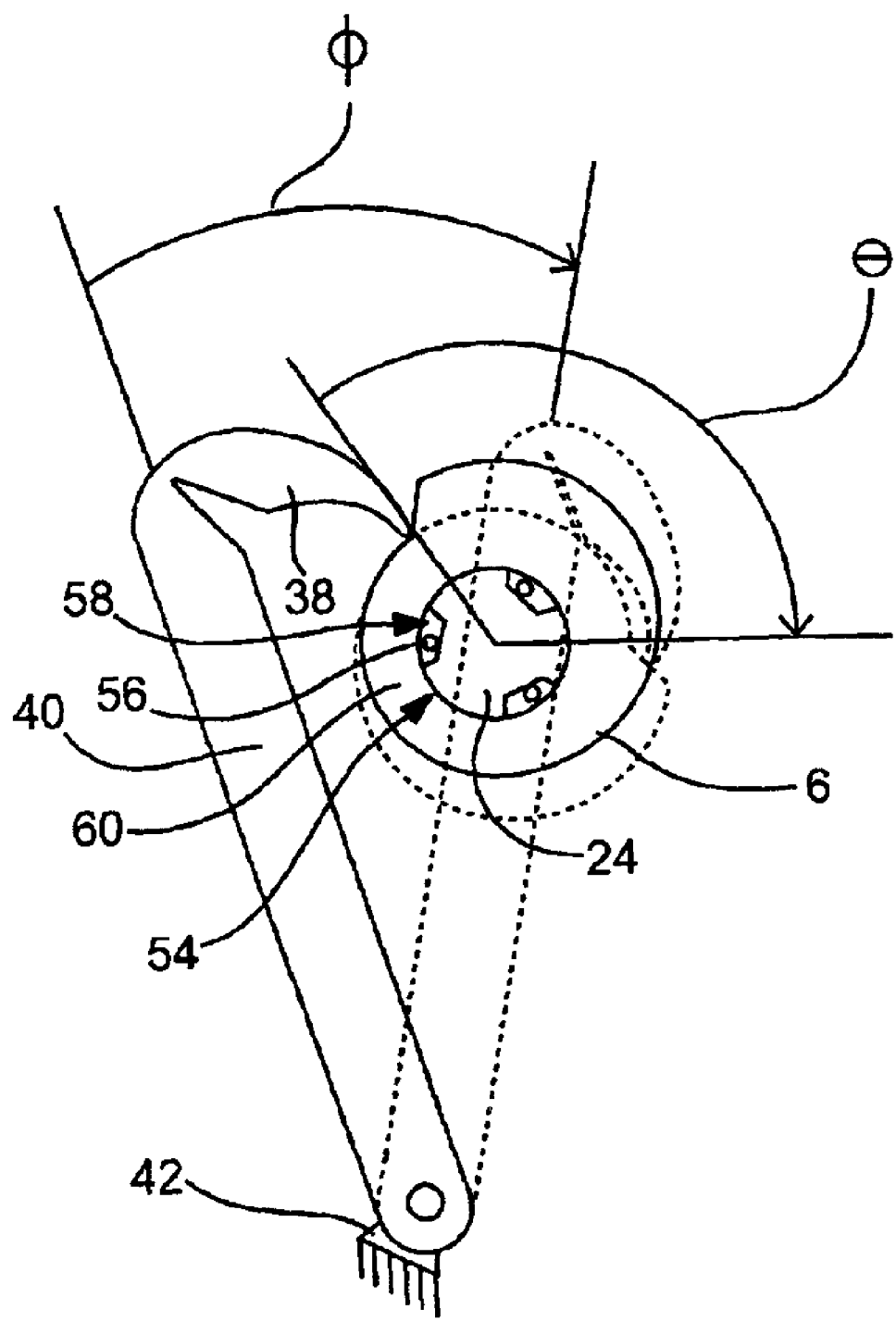
FIG. 3 is a front view of a preferred cocking mechanism in first and second stages of operation.

For such purposes, a clutch could equally well be included at the connector/crank interface or be provided for by a more sophisticated setup. The approach described is, however, preferred for its simplicity and ease of implementation. FIG. 3 shows a preferred implementation or crank member 6. A round body is provided instead of a typical elongate link member. Though not preferred, coupler 18 may be provided by a member having a shape different than shown as well. Yet using a round body for crank member 6 offers more room for a clutch bearing 24 and also enables such other features as discussed below. A pin or shoulder bolt affixed to housing 16 and running through the center of the clutch interfaces with the same to provide reaction forces to prevent rotation.

Of course, the direction in which rotation is permitted or the drive mechanism in general may be either clockwise or counterclockwise. FIGS. 1A–1E and 3, depict clockwise crank member movement in use.

Another common variation is to configure lance carrying member 10 as shown in FIG. 2 as opposed to as shown in FIGS. 1A–1E. In FIGS. 1A–1E, the shuttle or lance carrying member integrally includes the lance blade 12. In the variation in FIG. 2, lance carrying member 10 merely includes a receptacle section 26 to receive a snap-in disposable lance 28 such as One Touch® FinePoint™ lancets from LifeScan, Inc. (Milpitas, Calif.). It is common for such devices to have a twist-off or break-off safety cap to be removed to expose the lance tip before use. An interface post 62 may additionally or alternately be provided to retain a lancet. Yet another option is to use a conventional split collar device or style of loading. It is preferred, however, that the present invention employ a side or breach loading/removal approach as seen, for example, in U.S. Pat. No. 4,577,630.

Yet another optional feature shown in connection with the lance carrier in FIG. 2 is the presence outboard rails 30. When engaged with complimentary runners (not shown) the lance carrier 10 is both held down and permitted to move in and out with respect to a face 32 of the housing which abuts a users finger to be stuck as shown in FIG. 4 where the lance is indicated in phantom line.

Irrespective of such constructional details as to the linkage, drive 2 further includes a spring or biasing member 34. Force generated in the spring both fires the lance and retracts it at least partially so it does not pose a safety hazard. The spring shown is an extension spring. However, other types of springs may be used, including leaf springs, torsion springs and compression springs. The extension spring preferably comprises a coiled metal member, though an elastic member may be alternately employed.

Whatever the spring type or composition, one end is affixed or restrained to a spring support 36, which is preferably provided in connection with housing 16. Another end of the biasing member may be attached at the junction of the crank and coupler members as shown or along either member, for example, to produce a more compact design. This may be accomplished by looking a curved end of the extension spring about optional pin 20 or otherwise. In any case, the principles of the invention will not change, though the details of the particular device would.

The relative placement of the spring and slider-crank elements is of particular importance in the present invention. The members should be configured to as to affect the motion and function now described in connection with FIGS. 1A–1E. Details as to the specifics of the configuration may vary widely, but are well within the design and testing abilities of those ordinarily level of skill in the art.

First, FIG. 1A shows drive mechanism 2 in an uncocked position. In this position, lance tip 12 is partially withdrawn from its most advanced position shown in FIG. 1E. In this state (the state which the device returns by its own power to after firing), the extension spring is substantially aligned with the crank member pivots. Accordingly, it is at its shortest length and in its least-stressed position through the cycle of drive device 2.

Even in variation of the invention in which the type or relative locations of the spring and links vary (including the location of the association of the spring to the linkage members) there will be a state like that in FIG. 1A representing a minimum energy configuration for the spring in which it has release energy stored in cocking it to the extent possibly. With or without any clutch features as introduced above, such a state also represents a stable equilibrium position.

Figure 1B:
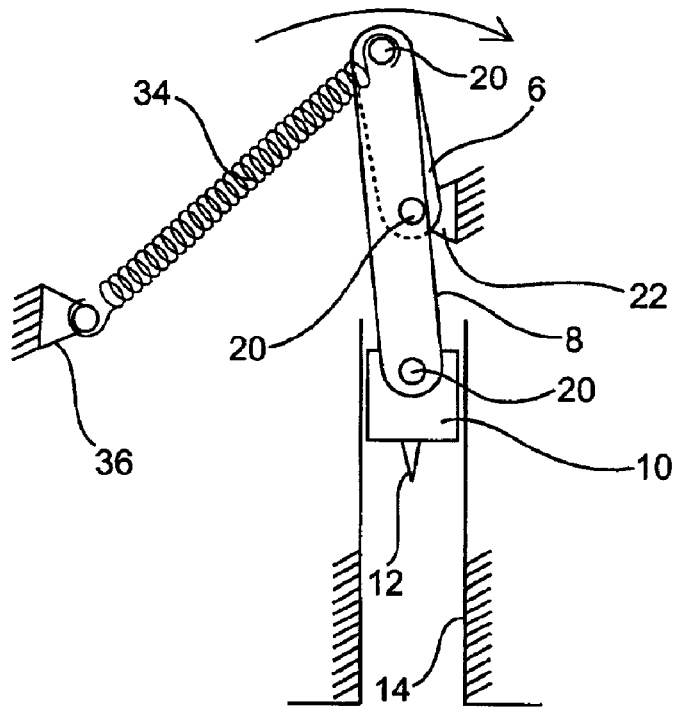

FIG. 1B shows the drive mechanism in the process of being cocked. Lance shuttle 10 is retracted as crank 6 is advanced, such as by user input. This in turn results in energy storage in spring 34. In the configuration of the invention shown, as the crank and coupler members approach alignment, the lance-carrying member reaches it most withdrawn state.

Figure 1C:
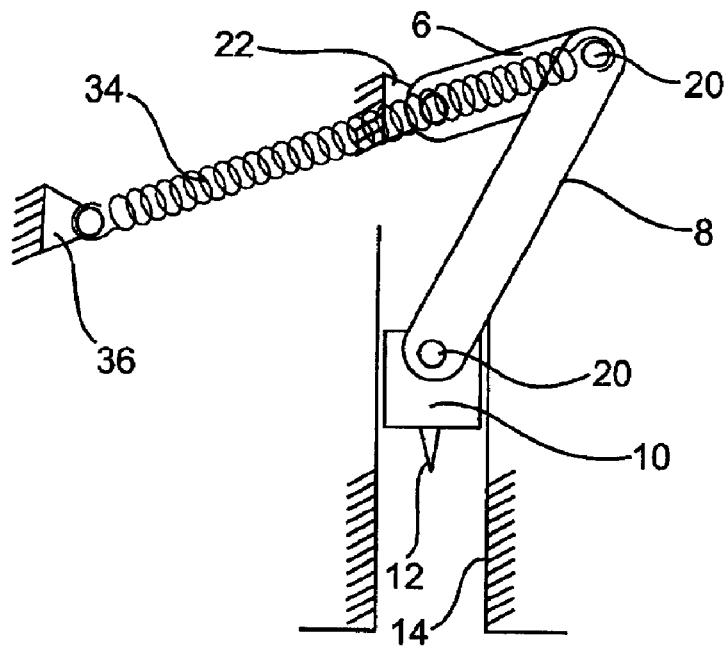

FIG. 1C shows drive mechanism 2 in a fully-cocked position. At this point, spring 34 reaches its maximum stored energy potential. The shuttle 10 has advanced slightly from its most retracted position but still has room in which to accelerate in firing before full extension and impacting a user's finger or other location. When fully cocked for firing, as shown in FIG. 1C, the system is in a state of unstable equilibrium. Advancement beyond the point of alignment will cause lance firing in a clockwise direction under the power of the spring. That is, when the spring goes "over-center" with respect to the crank, the firing motion commences.

Figure 1D:
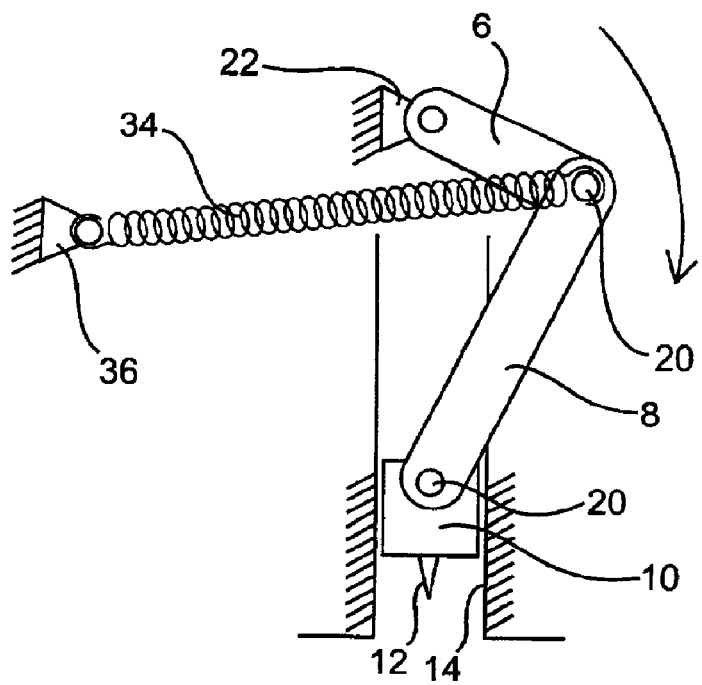

FIG. 1D illustrates this firing action. The large arrow dramatizes rapid movement in the direction indicated. After passing the unstable equilibrium or fully-cocked position in FIG. 1C where force applied by the spring has no moment arm to work on, as crank arm 6 progresses through its travel the spring is able to quickly draw the slider-crank mechanism though its prescribed motion.

Figure 1E:
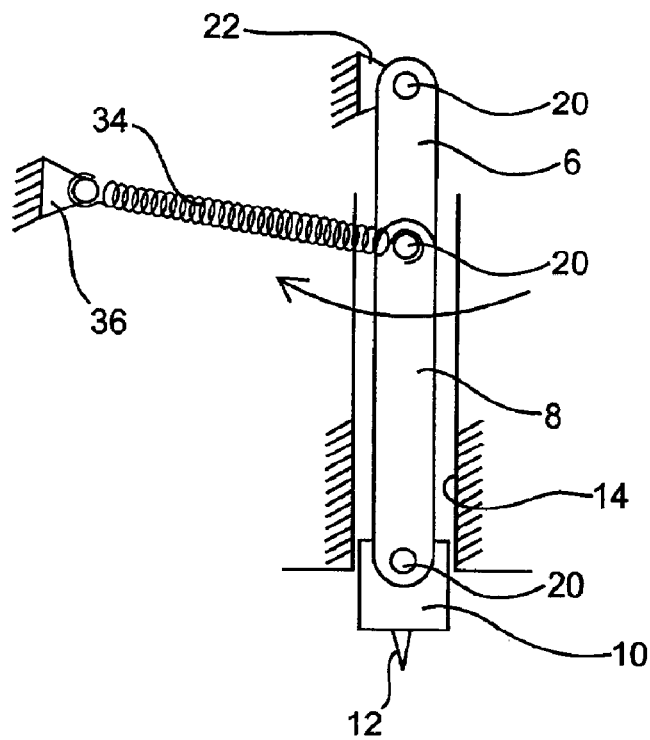

FIG. 1E show the maximum-extension point in the firing motion. Following this, spring 34 draws crank member 6 around so as to withdraw the lance end from the user's flesh. Again, by virtue of the length moment arm available for the spring to drive the crank, withdraw from firing occurs very rapidly as indicated by the arrow. Such action is further assisted by the inertia of the rotating crank. Accordingly, the transition between lancet puncture to withdraw occurs nearly instantaneously.

Beyond the actuation stage shown in FIG. 1E, the crank continues in the same direction as the spring continues to contract (or otherwise recover) until it swings the crank arm around to a position substantially as shown in FIG. 1A.

Of course, momentum imparted to the system by the spring in firing and retracting the lance may cause slight overrun. If no clutch is present, this can result in system oscillation. However, with a one-way clutch incorporated in the system, the drive advances to a given point possibly slightly loading the spring and is locked from returning the other direction.

In all, the drive provides a means for very rapid lance firing, followed by puncture and needle withdraw. In addition, its configuration lends itself to silent operation. By eliminating play in any connections, impulse loading that can produce noise is avoided.

A preferred manner of cocking the device to set such action in motion is shown in FIG. 3. As noted above, it shows crank member 6 configured as a wheel or disk. A recess 36 in the wheel is provided for receipt of the end of a pawl 38 in connection with an actuator in the form of a lever 40. It is shown in FIG. 4 as a depressible lever.

The lever arm pivots about a lever support 42, preferably provided in connection with housing 16. This action of lever 40 is depicted by the phantom-line illustration in FIG. 3. It shows movement of the lever arm by some angle $\Phi$. With pawl 38 engaged in with wheel 6 via a flat, recessed section or otherwise, the wheel is driven by such action through an angel $\theta$. Once the spring set to drive the crank goes over-center (passes the unstable equilibrium state of the drive mechanism 2), the crank will take-off and rotate on its own, firing the lance.

Preferably, the relation between the actuator elements shown in FIG. 3 is such that maximum travel of the lever results in surpassing the firing trigger point that frictional forces are not a factor, but not so far as to overly limit the amount of spring-powered rotation as to negatively effect the top speed of the lance.

Further, the lever, pawl and wheel forming a ratchet-type device are preferably configured so that the wheel easily over runs the pawl once it reaches an angular displacement prompting firing. Some bias of the pawl against the wheel may be required to ensure subsequent engagement. This may be provided by a spring member between the lever arm and pawl. As shown, the two items be formed by a unitary structure including a "living hinge," especially one including some resilience to provide for such bias.

Actually, a living hinge at the joint between coupler 8 and shuttle 10 and between lever 40 and support 42 may be advantageously employed as well. Of course, the rotable association between pawl 38 and lever 40 may be provided by a simple, pinned connection as shown elsewhere.

However the ratchet combination is configured, in use a user merely need depress the lever to take the system from an uncocked position, to cock and fire the lance. This turns operation into a one-step process. In other words, a user does not first have to cock and then release a catch to fire the device.

A preferred manner in which a user grasps and actuates the lancing mechanism of the present invention is illustrated in FIG. 4. After actuating lever 40 by applying force between the thumb 44 and one or more fingers 46, the housing face 32 is withdrawn from the target site 48, leaving a puncture or lance stick 50 to well-up a sample of blood.

The whole blood sample then may be tested using any number of a variety of analyte test strips 52 or another diagnostic instrument. Optional types of test strips may include those for measuring glucose levels, prothrombin time etc. Life Scan, Inc. (Milpitas, Calif.), produces a number of such analyte test strips preferably used in connection with the present invention.

CLAIMS

Though the invention has been described in reference to a certain examples, optionally incorporating various features, the invention is not to be limited to the set-ups described. The invention is not limited to the uses noted or by way of the exemplary description provided herein. It is to be understood that the breadth of the present invention is to be limited only by the literal or equitable scope of the following claims. In the claims, certain terms represent examples of lexicography. With respect to these, by a "linear path," it is mean a straight-line path or curvilinear path; by "lance-carrying structure," it is meant a member that integrally includes a lance blade or a member such as a housing or shuttle that receives a lance blade or a separate member that integrally includes a lance blade such as in the various disposable lance assemblies noted above; by "user," it is meant the recipient of lancing action, whether or not the individual is actuating the device; and by "actuator," it is meant a structural member such as a lever, pusher, handle, button, knob, pull string, cord or any other feature a user may grasp, pull or push to effect movement of communicative structure. That being said, I claim:

What is claimed is:

1. A lancing apparatus comprising:
    a housing, a crank member rotably attached to said housing at a first pivot location and a coupler rotably attached to said crank at a second pivot location, and a lance-carrying structure at a third pivot location, said lance-carrying structure being confined to a linear path relative to said housing,
    wherein a spring attached to said housing is positioned to force firing of said lance-carrying structure and return said lance-carrying structure to a retracted position, and
    wherein said lancing apparatus is configured to be cocked for firing by rotation of said crank about said first pivot location in the same direction said crank rotates to fire said lance-carrying structure.
2. The apparatus of claim 1, wherein said lance-carrying mechanism comprises a lance.
3. The apparatus of claim 1, wherein said lance-carrying mechanism comprises a lance and a lance shuttle.
4. The apparatus of claim 1, wherein said spring is an extension spring.
5. The apparatus of claim 1, wherein a first end of said spring is attached at said second pivot location.
6. The apparatus of claim 5, wherein said spring is and extension spring.
7. The apparatus of claim 6, wherein a second end of said spring is attached to said housing so as to only partially retract said lance-carrying structure.
8. The apparatus of claim 1, further comprising a ratchet combination configured to advance said crank member past a cocked position and allow substantially unrestricted firing of said lance-carrying structure.
9. The apparatus of claim 1, further comprising a clutch to only permit one-way rotation of said crank member.
10. A lancing apparatus comprising:
    a housing,
    a crank member rotably attached to said housing at a first pivot location,
    a coupler rotably attached to a lance-carrying structure at a second pivot location, said lance-carrying structure being confined to a straight-line path, and
    a spring attached between said housing and said second pivot location, wherein said spring is positioned to force firing of said lance-carrying structure upon passing an unstable equilibrium state and return said lance-carrying structure to a retracted position.
11. The apparatus of claim 10, wherein said lance-carrying structure comprises a lance.
12. The apparatus of claim 10, wherein said lance-carrying structure comprises a lance and a lance shuttle.
13. The apparatus of claim 10, wherein said spring is an extension spring.
14. The apparatus of claim 10, wherein said spring is attached to said housing so as to only partially retract said lance-carrying structure.
15. The apparatus of claim 10, further comprising a ratchet combination configured to rotate said crank member about said first pivot location in a direction past a cocked position and allow substantially unrestricted firing of said lance-carrying structure is the same direction.
16. The apparatus of claim 10, further comprising a clutch to only permit one-way rotation of said crank member.
17. The apparatus of claim 10, wherein said return of said lance-carrying structure results in a stable equilibrium state.
18. A method of actuating a lancing device, said method comprising:
    providing a lancing apparatus according to claim 1 or 10, wherein said lancing apparatus further comprises an actuator;
    turning said crank member in a single direction from an uncocked position, to a cocked position and beyond said cocked position,
    wherein firing said lance-carrying structure results from the turning of said crank beyond said cocked position.
19. The method of claim 18, wherein said lancing apparatus further comprises an actuator and said method further comprises:
    moving said actuator to turn said crank member.
20. The method of claim 18, wherein said lancing apparatus further comprises a ratchet combination and said method further comprises:
    engaging said ratchet combination to cock said lancing apparatus, and
    overrunning said combination in firing said lance-carrying structure.
21. The method of claim 18, further comprising:
    forming a lance stick in a user by said firing said lance-carrying structure.
22. The method of claim 21, further comprising:
    applying a blood sample formed at said lance stick to a test strip.

* * * * *